US012668785B2

(12) United States Patent
Carlsson et al.

(10) Patent No.: US 12,668,785 B2
(45) Date of Patent: Jun. 30, 2026

(54) COMBINATION TREATMENT BY ADMINISTERING A RECOMBINANT APYRASE PROTEIN IN CONJUNCTION WITH A $P2Y_{12}$ INHIBITOR

(71) Applicant: ASTRAZENECA AB, Södertälje (SE)

(72) Inventors: Leif Carlsson, Södertälje (SE); Sven Nylander, Södertälje (SE); Ola Fjellstrom, Södertälje (SE); Lina Badimon Maestro, Barcelona (ES)

(73) Assignee: ASTRAZENECA AB, Södertälje (SE)

( * ) Notice: Subject to any disclaimer, the term of this patent is extended or adjusted under 35 U.S.C. 154(b) by 145 days.

(21) Appl. No.: 18/352,414

(22) Filed: Jul. 14, 2023

(65) Prior Publication Data

US 2024/0026318 A1 Jan. 25, 2024

Related U.S. Application Data

(63) Continuation of application No. 17/405,670, filed on Aug. 18, 2021, now abandoned.

(60) Provisional application No. 63/067,388, filed on Aug. 19, 2020.

(51) Int. Cl.

| | |
|---|---|
| ***C12N 9/16*** | (2006.01) |
| ***A61P 7/04*** | (2006.01) |
| ***C07K 14/47*** | (2006.01) |
| *A61K 38/00* | (2006.01) |

(52) U.S. Cl.

CPC .................. *C12N 9/16* (2013.01); *A61P 7/04* (2018.01); *C07K 14/4703* (2013.01); *A61K 38/00* (2013.01); *C12Y 306/01005* (2013.01)

(58) Field of Classification Search

CPC ..... C12N 9/16; C12N 9/14; A61P 7/04; A61P 9/00; A61P 9/10; C07K 14/4703; A61K 38/001; A61K 31/4365; A61K 31/519; A61K 31/616; A61K 31/7076; A61K 45/06; A61K 38/46; A61K 31/7064; A61K 2300/00; C12Y 306/01005

See application file for complete search history.

(56) References Cited

FOREIGN PATENT DOCUMENTS

WO 2011088231 A1 7/2011

OTHER PUBLICATIONS

International Search Report and Written Opinion for International Application No. PCT/EP2021/072954, mailed Nov. 18, 2021, 18 Pages.

Moeckel D., et al., "Optimizing Human Apyrase to Treat Arterial Thrombosis and Limit Reperfusion Injury without Increasing Bleeding Risk", Science Translational Medicine, vol. 6, No. 248, Aug. 6, 2014, 248ra105, ISSN: 1946-6234, DOI: 10.1126/scitranslmed.3009246. pp. 1-24.

Pehrsson S., et al., Abstract 11146: AZD3366—an Optimized Recombinant Human Apyrase Combining Anti Platelet, Anti Inflammatory and Tissue Protective Actions with Low Bleeding Risk for Potential Mitigation of Thromboembolic Complications, Circulation, Nov. 11, 2019, 140:A11146, 5 Pages.

Sadowski M.I., et al., "The Sequence-Structure Relationship and Protein Function Prediction", Science Direct, Current Opinion in Structural Biology, vol. 19, 2009, pp. 357-362.

Seffernick J.L., et al., "Melamine Deaminase and Atrazine Chlorohydrolase: 98 Percent Identical but Functionally Different", Journal of Bacteriology, vol. 183, No. 8, Apr. 2001, pp. 2405-2410.

Singh R.K., et al., "Protein Engineering Approaches in the Post-Genomic Era", Current Protein and Peptide Science, vol. 19, No. 1, 2018, pp. 5-15.

Tang S., et al., "Identification of Dehalobacter Reductive Dehalogenases that Catalyse Dechlorination of Chloroform, 1, 1, 1-trichloroetahne and 1,1-dichloroethane", Philosophical Transactions of the Royal Society B, 2013, pp. 1-10.

Vilahur G., et al., Administration of a Soluble ADPase, AZD3366, on Top of Ticagrelor Confers Additional Cardioprotective Benefits to that of Ticagrelor Alone, Eur. Heart J., 2020, Downloaded from https://academic.oup.com/eurheartj/article/41/Supplement_2/ehaa946.3772/6005387, 1 page.

Wallentin L., et al., "Ticagrelor Versus Clopidogrel in Patients with Acute Coronary Syndromes", The New England Journal of Medicine, Sep. 10, 2009, vol. 361 No. 11, pp. 1045-1057.

Witkowski et al. "Conversion of a Beta-Ketoacyl Synthase to a Malonyl Decarboxylase by Replacement of the Active-Site Cysteine with Glutamine," Biochemistry, 1999, vol. 38, pp. 11643-11650.

*Primary Examiner* — Delia M Ramirez

(57) ABSTRACT

The present invention relates to methods for treating ischemic events in a patient, especially ST-segment elevation myocardial infarction and acute ischemic stroke, by administrating a recombinant apyrase protein in conjunction with a $P2Y_{12}$ inhibitor.

10 Claims, 2 Drawing Sheets

Specification includes a Sequence Listing.

COMBINATION TREATMENT BY ADMINISTERING A RECOMBINANT APYRASE PROTEIN IN CONJUNCTION WITH A $P2Y_{12}$ INHIBITOR

CROSS-REFERENCE TO RELATED APPLICATIONS

This application is a continuation of U.S. application Ser. No. 17/405,670, filed on Aug. 18, 2021, now abandoned, said U.S. application Ser. No. 17/405,670 which claims benefit under 35 U.S.C. § 119 (e) of the U.S. Provisional Application No. 63/067,388, filed Aug. 19, 2020. U.S. application Ser. No. 17/405,670 is incorporated by reference herein in its entirety for all purposes.

REFERENCE TO SEQUENCE LISTING SUBMITTED ELECTRONICALLY

This application incorporates by reference a Sequence Listing submitted with this application as text file entitled "201079-US-CNT.xml" created on Jul. 13, 2023 and having a size of 4,019 bytes.

FIELD OF THE INVENTION

The present invention relates to methods for treating ischemic events in a patient, especially ST-segment elevation myocardial infarction and acute ischemic stroke, by administering a recombinant apyrase protein in conjunction with a $P2Y_{12}$ inhibitor.

BACKGROUND

Myocardial infarction (MI) is a leading cause of hospital admissions and mortality around the world (Asaria et al. 2017). If left untreated, MI results in irreversible damage to the heart muscle due to a lack of blood flow (ischaemia) and thus oxygen. A primary goal of therapy with MI is therefore to expedite restoration of normal coronary blood flow with the aim of decreasing heart muscle damage through reperfusion therapy. Reperfusion therapy typically involves the use of therapeutics to increase blood flow and reduce thrombosis combined with surgical techniques such as percutaneous coronary intervention (PCI). Early reperfusion and PCI is preferable and associated with improved outcomes, with Guidelines suggesting PCI should be performed within 12 hours of MI symptom onset (Ibanez et al. 2018).

Several treatment strategies are available to deal with thrombus formation and fall into two classes-protein-based therapeutics and small molecule therapeutics. Examples of small molecule therapeutics include the $P2Y_{12}$ receptor inhibitors such as clopidogrel, ticagrelor, prasugrel and cangrelor, which are known for their ability to inhibit platelets and prevent blood clots. The effectiveness of both clopidogrel and ticagrelor in reducing cardiovascular morbidity and mortality in secondary prevention has been demonstrated in clinical trials and both drugs have been approved for use in the prevention of thrombotic events. For example, the National Institute for Health and Care Excellence (NICE) recommends ticagrelor in combination with low-dose aspirin for up to 12 months as a therapy for adults with acute coronary syndromes (ACS). These $P2Y_{12}$ receptor inhibitors do however come with an increased bleeding risk and therefore care does need to be taken to ensure that patients receive this treatment in accordance with the prescribing information and current guidelines.

Recent studies have investigated the use of recombinant apyrases as a protein-based therapeutic. Apyrases (ecto-ATP diphosphohydrolases) constitute a group of enzymes catalysing metabolism of ATP to ADP and ADP to AMP. In the body, the AMP produced by apyrase-induced hydrolysis of ATP and ADP is converted into adenosine by the ubiquitously expressed extracellular CD73/ecto-5'-nucleotidase. The first known human apyrase, CD39, was originally identified as a cell-surface protein on activated lymphocytes and endothelial cells and various in vitro and in vivo studies have shown apyrase is able to maintain vascular integrity and physiologically inhibit inflammation and thrombosis (Robson et al. 2005).

Apyrase reduces ATP and ADP interaction with all three platelet P2 receptors ($P2X_1$, $P2Y_1$ and $P2Y_{12}$), therefore acting to inhibit platelet activation and recruitment. In contrast to the small molecule inhibitors of $P2Y_{12}$ receptors, the use of apyrase to deplete ADP and ATP levels does not result in the increased levels of bleeding in preclinical models. Further to its anti-platelet effect, apyrase also has cardioprotective effects, which is understood to be mediated through i) the depletion of the pro-inflammatory ATP and ADP molecules; and ii) through the increased levels of the anti-inflammatory adenosine produced through apyrase action. More information of the mechanisms of action of endogenous apyrase is provided in FIG. 1 of Moeckel et al. (2014).

Moeckel et al. (2014) reports on the design and production of a recombinant optimised form of soluble CD39L3, a member of the human CD39 family. The resulting recombinant protein is termed 'APT102' or 'AZD3366'. The authors report that this recombinant protein exhibited four times higher adenosine diphosphatase activity and a 50 times longer plasma half-life than native apyrase and that treatment with APT102 in animal models decreased infarction size without an increase in bleeding time. The corresponding treatment with clopidogrel alone was not cardioprotective in this model whilst combining APT102 and clopidogrel treatment did not change the protective efficacy seen with APT102 alone (FIG. 6 of Moeckel et al. (2014)).

Despite optimal anti-platelet and anti-thrombotic treatment involving $P2Y_{12}$ receptor inhibitors such as ticagrelor, there is still around a 10% yearly risk of a new myocardial infarction event and increasing the intensity of these treatments increases bleeding risk without improving efficacy (Wallentin et al., 2009; Jernberg et al., 2015). Accordingly, there remains a need for effective and safe therapeutic methods that can be used in the treatment of an ischemic event such as a myocardial infarction. The present invention has been devised in light of the above considerations.

SUMMARY OF THE INVENTION

The present inventors have determined that administration of a recombinant apyrase protein in conjunction with a $P2Y_{12}$ inhibitor provides improved cardioprotective benefits compared to the individual use of $P2Y_{12}$ inhibitor alone. This suggests that the combined treatment can be used as an effective treatment of ischemic events in the heart such as myocardial infarction (e.g. ST-Elevation Myocardial Infarction) and ischemic events in the brain such as acute ischemic stroke and, for example, can be used to prevent or ameliorate injury resulting from the ischemic event (e.g. cardiac damage formed as a result of the myocardial infarction, or brain damage formed as a result of acute ischemic stroke).

In particular, the inventors demonstrated that administration of a recombinant apyrase protein (e.g. AZD3366) in conjunction with a $P2Y_{12}$ inhibitor (e.g. ticagrelor) was surprisingly effective at reducing infarct size and improving heart function in an animal model of myocardial infarction (MI). This is despite the results reported in FIG. 6 of Moeckel et al. (2014), which reports that use of a $P2Y_{12}$ inhibitor does not affect the cardioprotective effect observed with AZD3366 alone.

Furthermore, without wishing to be bound by theory, it is believed that the improved cardioprotective effect provided by the combination treatment is at least in part caused by the $P2Y_{12}$ inhibitor resulting in increased levels of extracellular adenosine. Since the cardioprotective effect of AZD3366 is reported to also involve increasing levels of extracellular adenosine, it was unexpected that the combined use of two agents ($P2Y_{12}$ inhibitor and recombinant apyrase protein) acting on the same pathway and modulating levels of the same end product would induce a greater cardioprotective effect than observed through the use of a single agent alone.

It was also determined that administering AZD3366 in conjunction with ticagrelor did not significantly increase bleeding levels in the animal model compared to ticagrelor alone. This is important, as it suggests that there would not be a significant additional risk in terms of increased bleeding in using the combination treatment compared to the use of $P2Y_{12}$ inhibitor alone, e.g. for treating those conditions that the $P2Y_{12}$ inhibitor is already approved for.

These results are in contrast to previous observations from clinical trials, where it has been consistently observed that increasing anti-platelet activity or increasing anti-thrombotic activity, on same or complementary pathways, increases risk of bleeding in combination with any beneficial efficacy effects.

As such, the proposed combination is unexpectedly a first example where net clinical benefit can be improved by targeting and enhancing effects attributable to the same biological pathway in settings such as MI.

Accordingly, one aspect of the present disclosure provides a method of treating an ischemic event in a patient, the method comprising administering a recombinant apyrase protein in conjunction with a $P2Y_{12}$ inhibitor.

In another aspect the present disclosure provides a recombinant apyrase protein for use in a method of treating an ischemic event in a patient, the method comprising administering the recombinant apyrase protein to the patient, wherein the recombinant apyrase protein is administered in conjunction with a $P2Y_{12}$ inhibitor.

In a further aspect, the present disclosure provides a recombinant apyrase protein and a $P2Y_{12}$ inhibitor for use in a method of treating an ischemic event in a patient, the method comprising administering the recombinant apyrase protein in conjunction with the $P2Y_{12}$ inhibitor to the patient.

In yet another aspect, the present disclosure provides a $P2Y_{12}$ inhibitor for use in a method of treating an ischemic event in a patient, the method comprising administering the $P2Y_{12}$ inhibitor to the patient, wherein the $P2Y_{12}$ inhibitor is administered in conjunction with a recombinant apyrase protein.

In another aspect, the present disclosure provides the use of a recombinant apyrase protein and/or a $P2Y_{12}$ inhibitor in the manufacture of a medicament for the treatment of an ischemic event in a patient, the treatment comprising administering the recombinant apyrase protein to the patient in conjunction with the $P2Y_{12}$ inhibitor.

The $P2Y_{12}$ inhibitor may be selected from the group consisting of ticagrelor, clopidogrel, ticlopidine, prasugrel, and cangrelor. In some embodiments, $P2Y_{12}$ inhibitor is selected from the group consisting of ticagrelor, clopidogrel and prasugrel. Preferably, the $P2Y_{12}$ inhibitor is ticagrelor or clopidogrel. Even more preferably, the $P2Y_{12}$ inhibitor is ticagrelor.

The recombinant apyrase protein may be a recombinant human CD39L3 apyrase, optionally a soluble recombinant human CD39L3 apyrase. The apyrase may be a soluble CD39L3 or an ADPase enhanced apyrase as described in any one of U.S. Pat. No. 7,247,300B1, EP2133430B1 and EP2523971B1. An exemplary recombinant human CD39L3 apyrase is provided here as SEQ ID NO: 2.

In some embodiments, the recombinant apyrase protein is a soluble CD39L3 protein comprising an amino acid sequence that is at least 80%, at least 85%, at least 90%, at least 95%, at least 96%, at least 97%, at least 98%, at least 99% identical to positions 49-485 of SEQ ID NO: 1, wherein the recombinant apyrase protein retains ADPase and ATPase activity. In some embodiments, the recombinant apyrase protein comprises one or more modifications (e.g. amino acid substitutions) compared with a reference apyrase, where said reference apyrase may be a wild-type apyrase (e.g. an apyrase having the amino acid sequence set forth in SEQ ID NO: 1) or a soluble apyrase (e.g. a soluble apyrase having the amino acid sequence set forth as position 49-485 of SEQ ID NO: 1).

These modification(s) may result in increased ADPase activity compared with the reference apyrase or the same ADPase activity as the reference apyrase combined with decreased ATPase activity as compared with the reference apyrase. In some embodiments, the one or more modifications may comprise or consist of substitutions at positions 67 and 69, wherein the positions are numbered according to SEQ ID NO: 1. The substitution at position 67 may be to a glycine and the substitution at position 69 may be to an arginine, or the substitution at position 67 may be to an alanine and the substitution at position 69 may be to an arginine. Preferably, the substitution at position 67 is to a glycine and the substitution at position 69 is to an arginine.

In some embodiments, the recombinant apyrase protein comprises an amino acid sequence that is at least 80%, at least 85%, at least 90%, at least 95%, at least 96%, at least 98%, at least 99% identical to the amino acid sequence set forth as SEQ ID NO: 2 (AZD3366). In particular exemplary embodiments, the recombinant apyrase protein comprises the amino acid sequence set forth as SEQ ID NO: 2.

In some cases, the patient may already be undergoing treatment with the $P2Y_{12}$ inhibitor when the ischemic event occurs. For example, the prescribing information for ticagrelor in treating acute coronary syndromes (ACS) describes initiating treatment with a 180 mg “loading” dose and then administering a “maintenance” dose of 90 mg twice daily during the first year after an ACS event and after one year administering 60 mg twice daily. Thus, the patient may have previously experienced a prior ischemic event in the past 2 years and is currently undergoing chronic treatment with the $P2Y_{12}$ inhibitor, e.g. by taking ticagrelor twice daily, when the ischemic event being treated here occurs. As noted above, despite optimal anti-platelet and anti-thrombotic treatment there still remains a risk of a new ischemic event occurring.

For example, patient may have received (been administered with) the $P2Y_{12}$ inhibitor in the preceding 72 hours, or preceding 36 hours, or preceding 48 hours, or preceding 24 hours, or preceding 20 hours, or preceding 16 hours, or preceding 12 hours, or preceding 8 hours, or preceding 6 hours prior to the present method being performed. In some embodiments, e.g. where the $P2Y_{12}$ inhibitor is ticagrelor, the patient has received the $P2Y_{12}$ inhibitor in the preceding 8-16 hours, e.g. 12 hours (i.e. as part of the maintenance dose administered twice daily).

In other cases, the patient may not be currently undergoing treatment with the $P2Y_{12}$ inhibitor. Such patients are described as "naïve" patients. This includes situations where the patient has never been administered the $P2Y_{12}$ inhibitor as well as situations where the patient has previously been administered the $P2Y_{12}$ inhibitor but no administrations have taken place for at least 24 hours, 48 hours, 72 hours or a week prior to the present method being performed.

In preferred embodiments, the method comprises administering the $P2Y_{12}$ inhibitor to the patient (e.g. a patient undergoing treatment with the, or another, $P2Y_{12}$ inhibitor, or a naïve patient) in addition to the recombinant apyrase protein. Typically, the method comprises administering the $P2Y_{12}$ inhibitor and recombinant apyrase protein as separate formulations that are administered separately, e.g. simultaneously or sequentially. A skilled physician or other skilled medical personnel can determine the most suitable manner of administering each therapeutic agent to the patient.

Where sequential administration is used, the recombinant apyrase protein and $P2Y_{12}$ inhibitor are preferably administered within 24 hours, 12 hours, 1 hour or more preferably within 30 minutes of each other. In some embodiments the recombinant apyrase protein is administered first, followed by the sequential administration of the $P2Y_{12}$ inhibitor. In other embodiments the $P2Y_{12}$ inhibitor is administered first, followed by the sequential administration of the recombinant apyrase protein.

In some embodiments, the ischemic event being treated is an acute coronary syndrome. Acute coronary syndromes include ST segment elevation myocardial infarction (STEMI), non-ST segment elevation myocardial infarction (NSTEMI) and unstable angina. In preferred embodiments, the ischemic events being treated is a ST segment elevation myocardial infarction (STEMI) in a patient.

As demonstrated herein, the combined administration of recombinant apyrase protein (e.g. AZD3366) and $P2Y_{12}$ inhibitor (e.g. ticagrelor) resulted in a cardioprotective effect in a preclinical animal model of myocardial infarction, where it reduced infarct size and improved cardiac function compared to placebo and treatment using the $P2Y_{12}$ inhibitor alone. As set out above, early reperfusion following myocardial infarction is preferable and associated with improved outcomes. Accordingly, administering apyrase protein in conjunction with the $P2Y_{12}$ inhibitor in patients suffering from an acute coronary syndrome (e.g. STEMI) should preferably be done as soon as possible following onset of the acute coronary syndrome and preferably as close as possible to the time when the patient undergoes percutaneous coronary intervention (PCI)).

In other embodiments, the ischemic event being treated is acute ischemic stroke. Every year, 100 new patients have an ischaemic stroke in a population of 70 000. Without treatment, 55 patients die or become dependent within a year. Most of the 100 patients have mild or transient stroke and receive only antiplatelet drugs to reduce recurrence. About 25-35 patients receive reperfusion therapy, which saves 5-6 patients from death or dependency and increases numbers with no disability. Therefore, it is an unmet clinical need to reduce morbidity and mortality associated with acute ischaemic stroke (AIS).

Preclinical and clinical trials have evaluated the use of $P2Y_{12}$ inhibitors and aspirin to treat and/or prevent stroke after an ischemic stroke event. Furthermore, preclinical data has demonstrated that the recombinant apyrase protein AZD3366 can be used to enhance reperfusion, reduce reocclusion and reduce intracerebral bleeding in animal models of ischemic stroke (Sun et al., 2011; Tan et al., 2014). It was therefore realised that the beneficial results in the preclinical myocardial infarction animal model described herein associated with the combined administration of AZD3366 and $P2Y_{12}$ inhibitor could also be beneficial in the treatment of ischaemic stroke. For example, the combination treatment may reduce infarct size and/or reduce brain damage in patients suffering from ischaemic stroke and achieve this effect without a significantly increased risk of bleeding compared to $P2Y_{12}$ inhibitors alone.

As described in more detail below, the time taken for onset of action for oral $P2Y_{12}$ inhibitors is typically several hours, meaning that even if the $P2Y_{12}$ inhibitor is administered very early after onset of the ischemic event (e.g. acute coronary syndrome), there is a period of several hours when the patient is not protected from associated damage (e.g. cardiac damage formed as a result of the myocardial infarction). In contrast, the recombinant apyrase protein AZD3366 has been shown in preclinical models to have high levels of activity within minutes of administration and to maintain this activity for more than 24 hours (Moekel et al. 2015) Thus, it was realised that administering the recombinant apyrase protein early, this would provide cardioprotective effects during the initial phase of the myocardial infarction before sufficient levels of the $P2Y_{12}$ inhibitor are bioavailable in the blood stream of the patient in order to exert a cardioprotective effect.

Thus, in some embodiments, the recombinant apyrase protein is administered to the patient in conjunction with the $P2Y_{12}$ 24 hours or less, or 18 hours or less, or 12 hours or less, or 6 hours or less, or 4 hours or less, or 2 hours or less, or 1 hour or less, or even 30 minutes or less after onset of the ischemic event (e.g. an acute coronary syndrome such as STEMI). In some embodiments the method further comprises carrying out surgical reperfusion therapy (e.g. PCI) on the patient less than 48 hours, less than 24 hours, less than 12 hours, less than 6 hours, less than 3 hours, less than 2 hours, or less than 1 hour following administering the recombinant apyrase protein in conjunction with the $P2Y_{12}$ inhibitor. In particular embodiments, the recombinant apyrase protein and $P2Y_{12}$ inhibitor remain bioavailable in the patient's blood stream during surgical reperfusion therapy (e.g. PCI).

In some embodiments, the recombinant apyrase protein is administered at a dose of 10 to 1000 mg.

In some embodiments, the $P2Y_{12}$ inhibitor is ticagrelor and is administered at a dose of between 60 to 200 mg, e.g. at 60 mg, 90 mg, 120 mg or 180 mg. In some embodiments, ticagrelor is administered at its recommended loading dose of 180 mg.

In some embodiments, the $P2Y_{12}$ inhibitor is clopidogrel and is administered at a dose of between 75 to 600 mg, e.g. at 75 mg, 150 mg, 225 mg, 300 mg, 375 mg, 450 mg, 525 mg or 600 mg. In some embodiments, clopidogrel is administered at its recommended loading dose of 300 mg or 600 mg.

In some embodiments, the $P2Y_{12}$ inhibitor is ticlopidine and is administered at a dose of 250 to 500 mg, e.g. at 250 mg or 500 mg. In some embodiments, ticlopidine is administered at its recommended loading dose of 500 mg.

In some embodiments, the $P2Y_{12}$ inhibitor is prasugrel and is administered at a dose of 5 to 60 mg, e.g. at 5 mg, 10 mg, 15 mg, 20 mg, 25 mg, 30 mg, 35 mg, 40 mg, 45 mg, 50 mg, 55 mg, or 60 mg. In some embodiments, ticlopidine is administered at its recommended loading dose of 60 mg.

In some embodiments the $P2Y_{12}$ inhibitor is cangrelor and is administered at a dose of 30 μg/kg intravenous bolus followed by 4 μg/kg per minute intravenous infusion.

In some embodiments, the method further comprises administering aspirin to the patient, e.g. such that the recombinant apyrase protein is administered in conjunction with the $P2Y_{12}$ inhibitor and aspirin. In these embodiments, the method typically comprises administering the recombinant apyrase protein, $P2Y_{12}$ inhibitor and aspirin as separate formulations that are administered separately, e.g. simultaneously or sequentially. The aspirin may be administered at a dose of 50 to 325 mg.

Another aspect of the invention relates to a kit comprising the recombinant apyrase protein and the $P2Y_{12}$ inhibitor described herein, optionally wherein the kit further comprises aspirin.

The invention includes the combination of the aspects and preferred features described except where such a combination is clearly impermissible or expressly avoided.

SUMMARY OF THE FIGURES

Embodiments and experiments illustrating the principles of the invention will now be discussed with reference to the accompanying figures in which.

DETAILED DESCRIPTION OF THE INVENTION

Figure 1:
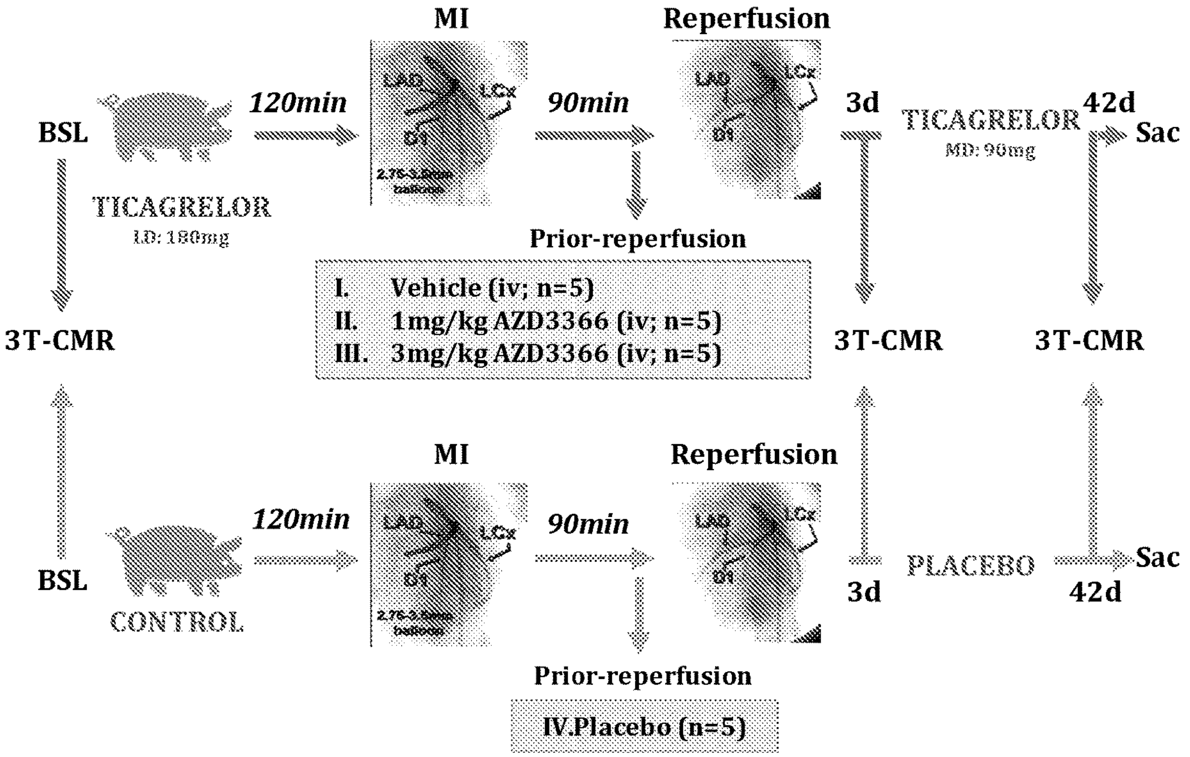
FIG. 1 illustrates the experimental protocol used to examine whether administration of recombinant apyrase protein AZD3366 confers additional benefits to that of ticagrelor alone in terms of reduced infarct size and improved heart function in a pig animal model of myocardial infarction. BSL=baseline; MI=myocardial infarction; Sac=sacrifice; CMR=Cardiac Magnetic Resonance assessment.

Aspects and embodiments of the present invention will now be discussed with reference to the accompanying figures. Further aspects and embodiments will be apparent to those skilled in the art. All documents mentioned in this text are incorporated herein by reference.

Recombinant Apyrase Proteins

An apyrase (EC 3.6.1.5) catalyses the hydrolysis of phosphoanhydride bonds of adenosine triphosphate (ATP) to adenosine monophosphate (AMP) and adenosine diphosphate (ADP) to AMP. CD39 family members (also termed ecto-nucleoside triphosphate diphosphohydrolase (E-NTP-Dase) family members) represent some of the best characterised apyrases. Human CD39 family members include the native proteins set out in the following table:

| Name of native protein | Additional names | NCBI accession number |
|---|---|---|
| CD39 | ATPDase, ecto-apyrase, NTPDase1 | U87967.1 |
| CD39L1 | NTPDase2, ecto-ATPase | AF144748.1 |
| CD39L2 | NTPDase6 | AY327581.1 |
| CD39L3 | NTPDase3, CD39L3, HB6 | AF034840.2 |
| CD39L4 | NTPDase5,ER-UDPase, PCPH | AF039918.1 |
| LALP70 | UDPase, NTPDase4 | AF016032.1 |
| LALP1 | NTPDase7 | AF269255.1 |
| liver canalicular ecto-ATPase | NTPDase8, hATPDase | AY430414.1 |

In some embodiments, the recombinant apyrase protein is a recombinant human apyrase protein or an engineered version thereof. In some embodiments, the recombinant apyrase protein is a member of the CD39 family, e.g. any of the native proteins set forth in the above table, or an engineered version thereof.

The recombinant apyrase protein may be a soluble recombinant human apyrase protein, e.g. an apyrase protein that lacks some or all of the amino acid residues that make up a transmembrane domain of the apyrase protein, which may be a member of the CD39 family. For example, human CD39L3 is a 529 amino acid residue protein shown in SEQ ID NO: 1. A particular exemplary soluble CD39L3 apyrase protein has the amino acid sequence set forth as position 49-485 of SEQ ID NO: 1.

The term "engineered" or "engineered version thereof" in the context of recombinant apyrase proteins means that the engineered protein has a similar, but not identical, amino acid sequence to a reference apyrase protein. A reference apyrase protein may be a wild-type apyrase protein (e.g. the full-length CD39L3 apyrase protein) or a soluble apyrase protein (e.g. the a protein that has the amino acid sequence set forth as position 49-485 of SEQ ID NO: 1). The engineered recombinant apyrase protein may comprise one or more amino acid substitutions, e.g. a substitution that alters the enzymatic activity (e.g. ADPase activity) compared to the reference apyrase, and/or a functionally conservative substitution that does not substantially alter the enzymatic activity of the reference apyrase. An engineered recombinant apyrase protein may have an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to the reference apyrase protein. For example, the recombinant apyrase protein set forth in SEQ ID NO: 2 (AZD3366) is an engineered version of the soluble CD39L3 apyrase protein having the amino acid sequence set forth as position 49-485 of SEQ ID NO: 1.

In a preferred embodiment, the recombinant apyrase protein is a CD39L3 protein or an engineered version thereof. The recombinant apyrase protein may have an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 1. In an even more preferred embodiment, the recombinant apyrase protein is a soluble CD39L3 protein or an engineered version thereof. The recombinant apyrase protein may have an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to the amino acid sequence set forth as position 49-485 of SEQ ID NO: 1.

The design, production and use of soluble recombinant apyrase proteins including engineered versions of CD39L3 (e.g. enhanced apyrases) are described in U.S. Pat. No. 7,247,300B1, EP2133430B1 and EP2523971B1, all of which are incorporated herein by reference in their entireties. The recombinant apyrase protein described herein may be any of the apyrases described in those publications.

EP2133430B1 describes ADPase enhanced apyrases. These ADPase enhanced apyrases comprise modified forms of reference apyrases, wherein the modification results in increased ADPase activity compared with the reference apyrase or the same ADPase activity as the reference apyrase combined with decreased ATPase activity as compared with the reference apyrase. Exemplary ADPase enhanced apyrases include those comprising substitutions at positions 67 and 69 of CD39L3, wherein the position numbering is in accordance with SEQ ID NO: 1. Specifically, ADPase enhanced apyrases include protein 8742, comprising R67G and T69R substitutions; and protein 8906, comprising R67A and T69R substitutions, as described in EP2133430B1.

Exemplary ATPase and ADPase assays used to determine this activity are disclosed in EP2133430B1. For example, ATPase and ADPase enzyme activities of purified soluble ADPase enhanced apyrases can be determined at 37° C. in a 1 ml solution containing 8 mM $CaCl_2$), 200 μM substrate (ATP for ATPase or ADP for ADPase), 50 mM imidazole, and 50 mM Tris, pH 7.5 (Picher, et al., Biochem. Pharmacol. (1938) 51:1453). The reaction can be stopped and inorganic phosphate released can be measured by addition of 0.25 ml of malachite green reagent (Baykov, et al., Anal. Biochem. (1988) 171:266). Based on the spectrophotometric analysis at 630 nm, one unit of ATPase (or ADPase) corresponds to release of 1 μmole of inorganic phosphate/min at 37° C. Key kinetic constants for the enzyme such as Km and kcat may be obtained by fitting data into, for example, a Michaelis-Menten equation. Other assays useful for monitoring biochemical function include, but are not limited to, a radiometric assay, a HPLC assay both described by Gayle III, et al. (J. Clin Invest. (1998) 101:1851-1859) or a radio-TLC assay described by Marcus, A. J., et al. (J. Clin Invest. (1991) 88:1690-1696).

Thus, the recombinant apyrase protein described herein may comprise one or more modifications (e.g. amino acid substitutions) compared with a reference apyrase having the amino acid sequence set forth as positions 49-485 of SEQ ID NO: 1 (i.e. a soluble version of CD39L3). These modification(s) may result in increased ADPase activity compared with the reference apyrase or the same ADPase activity as the reference apyrase combined with decreased ATPase activity as compared with the reference apyrase. In some embodiments, the one or more modifications may comprise or consist of substitutions at positions 67 and 69, wherein the positions are numbered according to SEQ ID NO: 1. The substitution at position 67 may be to a glycine and the substitution at position 69 may be to an arginine, or the substitution at position 67 may be to an alanine and the substitution at position 69 may be to an arginine. Preferably, the substitution at position 67 is to a glycine and the substitution at position 69 is to an arginine.

EP2523971B1 describes apyrases and methods of producing apyrases that comprise a homogeneous N-terminus, e.g. such that more than 80% of the apyrase molecules have the same N-terminus which comprises EVLP. These proteins with a homogenous N-terminus are described as having an average isoelectric point in the range of 3.0 to 4.5 and/or having enhanced half lives in rabbits and pigs.

Thus, the recombinant apyrase protein described herein may comprise a homogenous N-terminus such that more than 80% of the apyrase molecules have the same N-terminus, which N-terminus is EVLP, as described in EP2523971B1.

In certain embodiments, the recombinant apyrase protein may further comprise one or more functionally conservative substitutions (e.g. in addition to the substitutions in the ADPase enhanced apyrases described above). Functionally conservative substitutions are substitutions that do not affect (or do not substantially affect) one or more functional properties (e.g. enzymatic activity) as compared to the equivalent unsubstituted protein. In some embodiments the recombinant apyrase protein comprises 1, 2, 3, 4, 5, 6, 7, 8, 9, 10, 11, 12, 13, 14, 15, 16, 17, 18, 19 or 20 functionally conservative substitutions.

In preferred embodiments, the recombinant apyrase protein comprises an amino acid sequence that is at least 80%, 81%, 82%, 83%, 84%, 85%, 86%, 87%, 88%, 89%, 90%, 91%, 92%, 93%, 94%, 95%, 96%, 97%, 98%, 99% or 100% identical to SEQ ID NO: 2, optionally wherein the amino acid residue at position 67 is a glycine and the amino acid residue at position 69 is an arginine, wherein the positions are numbered according to SEQ ID NO: 1. For example, the recombinant apyrase protein may comprise the amino acid sequence of SEQ ID NO: 2 with 1 or more (e.g. 1, 2, 3, 4, 5, 6, 7, 8, 9, 10, 11, 12, 13, 14, 15, 16, 17, 18, 19 or 20) functionally conservative substitutions, optionally wherein the amino acid residue at position 67 is a glycine and the amino acid residue at position 69 is an arginine, wherein the positions are numbered according to SEQ ID NO: 1. For the avoidance of doubt, amino acid residue positions 67 and 69 according to SEQ ID NO: 1 correspond to amino acid residue positions 19 and 21 respectively according to SEQ ID NO: 2. In exemplary embodiments, the recombinant apyrase protein comprises the amino acid sequence of SEQ ID NO: 2.

$P2Y_{12}$ Inhibitors

The $P2Y_{12}$ inhibitor may be selected from a list consisting of: ticagrelor, clopidogrel, ticlopidine, prasugrel, and cangrelor. Reference herein to $P2Y_{12}$ inhibitor includes any of these compounds as well as any metabolites, e.g. active metabolites. In some embodiments, the $P2Y_{12}$ inhibitor may be selected from a list consisting of: ticagrelor, clopidogrel, ticlopidine and prasugrel, e.g. selected from the list consisting of ticagrelor, clopidogrel and prasugrel. In preferred embodiments, the $P2Y_{12}$ inhibitor may be ticagrelor or clopidogrel. In particularly preferred embodiments, the $P2Y_{12}$ inhibitor is ticagrelor.

Ticagrelor [(1S,2S,3R,5S)-3-[7-[[(1R,2S)-2-(3,4-difluorophenyl)cyclopropyl]amino]-5-(propylthio)-3H-1,2,3-triazolo[4,5-d]pyrimidin-3-yl]-5-(2-hydroxyethoxy)-1,2-cyclopentanediol] is a reversibly binding oral P2Y (12) receptor antagonist in development for the prevention of thrombotic events in patients with acute coronary syndromes. It has the following chemical structure:

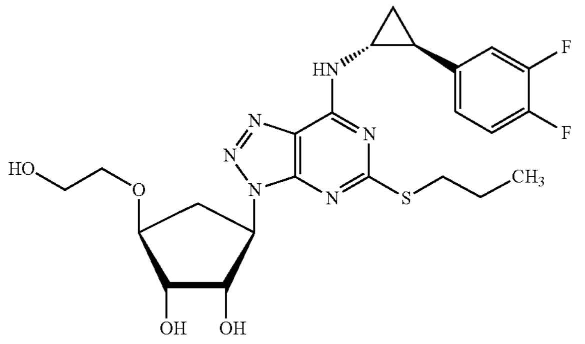

Ticagrelor is the active ingredient in the drug product known as BRILINTA® (or BRILIQUE in Europe) which has been approved for use in multiple jurisdictions including the USA and Europe. Ticagrelor is currently marketed in the form of 60 mg and 90 mg immediate release tablets. WO 2008/024045 discloses certain pharmaceutical formulations containing ticagrelor for oral administration. WO 2017/182589 discloses rapidly disintegrating oral dosage forms of ticagrelor.

Ticagrelor is typically rapidly absorbed after oral administration. Unlike clopidogrel and prasugrel, ticagrelor is not a prodrug and does not require metabolic activation for activity. Still, ticagrelor is extensively metabolised, with ticagrelor and its active and approximately equipotent metabolite (AR-C124910XX), comprising the major circulating components in the plasma. Plasma concentrations of ticagrelor and its active metabolite increase in a dose-dependent manner; peak concentrations achieved within approximately 1.5 and 2.5 hours, respectively. Maximum inhibition of platelet aggregation is observed approximately 2 hours after a dose and this is maintained for more than 8 hours after a dose. The mean elimination half-lives for ticagrelor and its active metabolite are described in the drug label as 7 hours and 9 hours, respectively. Following discontinuance, platelet activity returns to baseline after 5 days.

In preferred embodiments, ticagrelor is administered orally as a 180 mg loading dose in conjunction with the recombinant apyrase protein. Ticagrelor may be administered in an orodispersible tablet (ODT) form, e.g. as described in WO 2017/182589. One or more subsequent maintenance doses may be administered after the loading dose, e.g. without the recombinant apyrase protein. As described above, following an initial loading dose of 180 mg, the prescribing information for ticagrelor describes administering a maintenance dose of 90 mg twice daily during the first year after an ACS event and after one year administering 60 mg twice daily. The one or more subsequent maintenance doses may comprise twice daily doses of 90 mg of ticagrelor, or twice daily doses of 60 mg of ticagrelor. The prescribing information further describes administering ticagrelor with daily maintenance doses of aspirin of 75-100 mg. Accordingly, the one or more subsequent maintenance doses may further comprise administering daily doses of aspirin of 75-100 mg.

The $P2Y_{12}$-receptor inhibitor may be clopidogrel. Clopidogrel is typically administered via oral route. In some embodiments, clopidogrel is administered as a 300 mg or 600 mg loading dose in conjunction with the recombinant apyrase protein. One or more subsequent maintenance doses may comprise about 75 mg of clopidogrel and may be administered after the loading dose, e.g. without the recombinant apyrase protein. As with ticagrelor above, the maintenance doses of clopidogrel may be administered daily doses of aspirin of 75-100 mg.

Clopidogrel is a prodrug and requires metabolic activation for its activity. Peak plasma concentrations of the active metabolite occur approximately 30-60 minutes following an oral dose, with dose-dependent platelet aggregation inhibition observed in around 2 hours following administration. Following oral administration of a single dose, dose-dependent platelet aggregation inhibition can be observed in 2 hours. Clopidogrel has an elimination half-life of approximately 6 hours following a single dose of 75 mg, whilst its active metabolite has an elimination half-life of approximately 30 minutes. After discontinuance, platelet aggregation and bleeding times gradually return to baseline in about 5 days.

The $P2Y_{12}$-receptor inhibitor may be prasugrel. Prasugrel is typically administered via oral route. In some embodiments, prasugrel is administered as a 60 mg loading dose in conjunction with the recombinant apyrase protein. One or more subsequent maintenance doses may comprise about 5 mg or 10 mg of prasugrel and may be administered after the loading dose, e.g. without the recombinant apyrase protein. As with ticagrelor above, the maintenance doses of prasugrel may be administered with daily doses of aspirin of 75-100 mg.

Prasugrel is a prodrug and rapidly metabolised to a pharmacologically active metabolite. Peak plasma concentrations of the active metabolite occur approximately 30 minutes after dosing. It has an elimination half-life of about 7.4 hours.

The $P2Y_{12}$-receptor inhibitor may be ticlopidine. Ticlopidine is typically administered via oral route. In some embodiments, ticlopidine is typically administered via oral route. In some embodiments, ticlopidine is administered as a 500 mg loading dose in conjunction with the recombinant apyrase protein. One or more subsequent maintenance doses may comprise about 250 mg of ticlopidine and may be administered after the loading dose, e.g. without the recombinant apyrase protein. As with ticagrelor above, the maintenance doses of ticlopidine may be administered daily doses of aspirin of 75-100 mg.

Peak plasma levels of ticlopidine are typically observed around 2 hours after oral administration. Half-life following a single dose ranges from 7 to 13 hours. Half-life following repeated dosing is about 4 to 5 days.

The $P2Y_{12}$-receptor inhibitor may be cangrelor. Cangrelor may be administered intravenously as a bolus, as a continuous infusion, or as a bolus followed by a continuous infusion. In some embodiments. cangrelor is administered as a 30 μg/kg intravenous bolus followed immediately by 4 μg/kg per minute intravenous infusion.

Cangrelor rapidly reaches steady state plasma levels and platelet aggregation inhibition within 30 min of onset of infusion and the plasma half-life is short, being approximately less than 9 min. Maximal platelet inhibition is achieved within 15 min. The elimination half-life of cangrelor is about 3-6 minutes and platelet responses typically return to baseline within 15 minutes of discontinuation.

Treatment and Administration

The methods and products for use described herein are for treating an ischemic event in a patient (e.g. a human patient), which includes diseases and disorders where the blood supply is restricted to a particular part of the patient's body, e.g. the patient's heart or brain, where the restriction may be caused by a blood clot (thrombus). Ischemic events in the heart include an acute coronary syndrome. Ischemic events in the brain include acute ischemic stroke (AIS). Acute coronary syndromes include myocardial infarctions classified as ST segment elevation myocardial infarction (STEMI) or non-ST segment elevation myocardial infarction (NSTEMI), and unstable angina. In preferred embodiments, the treatment is a treatment of a ST segment elevation myocardial infarction (STEMI) in a patient.

Myocardial infarctions are generally clinically classified into STEMI and NSTEMI. These are based on changes to an electrocardiogram (ECG) and can be diagnosed by a physician or other skilled medical personnel. The type of myocardial infarction may be as defined in accordance with or derived from the universal definition of myocardial infarction set out in Thygesen et al. 2018.

In the therapeutic methods described herein, the recombinant apyrase protein is administered in conjunction with the $P2Y_{12}$ inhibitor. Use of the term "in conjunction" is this context is intended to mean that following administration (e.g. within 30 minutes, or within an hour, or within 2 hours, or within 3 hours), both the $P2Y_{12}$ inhibitor (and/or a metabolite thereof) and recombinant apyrase protein are bioavailable (i.e. have an active effect) in the blood stream of the patient. In animal models, administration of the recombinant $P2Y_{12}$ inhibitor AZD3366 becomes active within 5 minutes and does not return to baseline for 3 to 4 weeks, whereas it typically takes longer for $P2Y_{12}$ inhibitors to become active following administration. For example, maximum activity of ticagrelor is not normally observed until around 2 hours after a dose and this is maintained for more than 8 hours.

Accordingly, it is not always necessary for both the recombinant apyrase protein and the $P2Y_{12}$ inhibitor to be physically administered at the same time in order for the recombinant apyrase protein to administered in conjunction with the $P2Y_{12}$ inhibitor. Rather, the one of the recombinant apyrase protein and $P2Y_{12}$ inhibitor may be administered first, followed by the other agent being administered later (e.g. an hour or more later) provided that following administration both the recombinant apyrase protein and $P2Y_{12}$ inhibitor are bioavailable in the blood stream of the patient.

Furthermore, some patients exhibiting an ischemic event may already be regularly administering a $P2Y_{12}$ inhibitor, e.g. as part of a maintenance doses following a previous ischemic event. Such patients are referred to herein as "currently undergoing treatment with a $P2Y_{12}$ inhibitor". For example, 90 mg doses of ticagrelor are typically administered twice daily as part of maintenance doses. In such patients that are administered with the recombinant apyrase protein according to the method herein, it may not always be necessary to administer another dose of the $P2Y_{12}$ inhibitor because the inhibitor (and/or a metabolite thereof) is still considered bioactive in the blood stream of the patient. Alternatively, a reduced dose than the normal loading dose of the $P2Y_{12}$ inhibitor may be administered in order to top up the levels of bioactive $P2Y_{12}$ inhibitor in the blood stream. E.g. in the case of ticagrelor, a dose of 60 mg or 90 mg or 150 mg may be administered if ticagrelor is still bioactive in the patient's blood stream, as opposed to a typical loading dose of 180 mg. Effective dosages may be determined by a skilled physician or other skilled medical personnel. Preferably, however, even if the patient is currently undergoing treatment with a $P2Y_{12}$ inhibitor, the method still comprises administering the $P2Y_{12}$ inhibitor (e.g. a loading dose) to the patient.

A $P2Y_{12}$ inhibitor may still be considered bioactive in the blood stream in the patient if the last dose of the inhibitor was administered within a time period corresponding to the mean elimination half-life of the $P2Y_{12}$ inhibitor, more than twice the mean elimination half-life of the $P2Y_{12}$ inhibitor, or more than three times the mean elimination half-life of the $P2Y_{12}$ inhibitor, or more than five times the mean elimination half-life of the $P2Y_{12}$ inhibitor. For example, in the case of ticagrelor the mean elimination half-life is 7 hours for ticagrelor and 9 hours for its active metabolite. Accordingly, ticagrelor may be considered bioactive in the blood stream in the patient if the last dose was within the last 9 hours, within the last 18 hours, within the last 27 hours, within the last 36 hours, or within the last 45 hours. Alternatively, the $P2Y_{12}$ inhibitor may be considered bioactive in the blood stream until activity returns to baseline following discontinuance of dosing, which in the case of ticagrelor is after 5 days.

Other patients exhibiting an ischemic event may not have previously been administered a $P2Y_{12}$ inhibitor, or may have discontinued previous $P2Y_{12}$ inhibitor administration, e.g. such that the $P2Y_{12}$ inhibitor is no longer considered bioactive in the patient's blood stream. These patients may be referred to as "naïve" patients. In naïve patients, in order to administer the recombinant apyrase protein in conjunction with the $P2Y_{12}$ inhibitor, it is necessary for the method to comprise a step of administering the $P2Y_{12}$ inhibitor to the patient.

The recombinant apyrase protein and $P2Y_{12}$ inhibitor may be administered as a combined formulation, e.g. via intravenous injection. Alternatively, administration of the recombinant apyrase protein and $P2Y_{12}$ inhibitor to the patient may be simultaneous or sequential. Simultaneous administration as used herein refers to the administration of both the recombinant apyrase protein and $P2Y_{12}$ inhibitor to the patient at essentially the same time (e.g. within 10 minutes, within 5 minutes, or within 1 minute of each other), optionally via different administration routes. For example, intravenous injection of the recombinant apyrase protein within 1 minute of the $P2Y_{12}$ inhibitor being provided by oral administration would be considered simultaneous administration.

Where sequential administration is used, the recombinant apyrase protein and $P2Y_{12}$ inhibitor are preferably administered within 24 hours, 18 hours, 12 hours, 6 hours, 2 hours, 1 hour or more preferably within 30 minutes of each other. In some embodiments the recombinant apyrase protein is administered first, followed by the sequential administration of the $P2Y_{12}$ inhibitor. In other embodiments the $P2Y_{12}$ inhibitor is administered first, followed by the sequential administration of the recombinant apyrase protein.

In some embodiments, the recombinant apyrase protein is administered to the patient in conjunction with the $P2Y_{12}$ inhibitor 24 hours or less, or 18 hours or less, or 12 hours or less, or 6 hours or less, or 4 hours or less, or 2 hours or less, or 1 hour or less, or even 30 minutes or less after onset of the ischemic event (e.g. acute coronary syndrome such as STEMI). Onset of the ischemic event as referred to herein may be at the onset of one or more symptoms of the ischemic event (e.g. chest pain in the case of STEMI) or at the time of diagnosis, (e.g. via electrocardiogram in the case of acute coronary syndrome), which may be carried out prior to or shortly after the patient arrives at a hospital (or equivalent thereof) for treatment.

Preferably, the patient is administered with the recombinant apyrase protein in conjunction with the $P2Y_{12}$ inhibitor prior to surgical reperfusion therapy (e.g. percutaneous coronary intervention (PCI)) being performed on the patient suffering from the acute coronary syndrome.

PCI may comprise, without limitation, balloon angioplasty, stent implantation, rotational or laser atherectomy, and/or brachytherapy. In instances in which a stent is implanted, the stent may be, without limitation, a bare-metal stent, a drug-eluting stent, an absorbable stent, etc., as known in the art.

The cardioprotective effect provided by the combination of recombinant apyrase protein and $P2Y_{12}$ inhibitor may be useful to prevent and/or alleviate any injury to cardiac tissue or function attributed to the restoration of circulation following reperfusion therapy. Thus, in some embodiments the method further comprises carrying out surgical reperfusion therapy (e.g. PCI) on the patient less than 48 hours, less than 24 hours, less than 12 hours, less than 6 hours following administering the recombinant apyrase protein. In some embodiments, the recombinant apyrase protein and the $P2Y_{12}$ inhibitor are both administered to the patient before carrying out surgical reperfusion therapy (e.g. PCI). In other embodiments, the recombinant apyrase protein is administered to the patient before carrying out surficial reperfusion therapy (e.g. PCI) and the $P2Y_{12}$ inhibitor is administered shortly after, e.g. within 6 hours, within 4 hours, within 2 hours, or within 1 hour of the surgical reperfusion therapy being performed. In some embodiments, the recombinant apyrase protein and $P2Y_{12}$ inhibitor remain bioavailable in the patient's blood stream during surgical reperfusion therapy (e.g. PCI).

The disclosure includes embodiments where any of the timings described above regarding i) simultaneous or sequential administration of the recombinant apyrase protein and the $P2Y_{12}$ inhibitor; ii) timing of administration in relation to the onset of the ischemic event; and iii) timing of administration in relation to the surgical reperfusion therapy (e.g. PCI) are combined. For example, the method may comprise administering the recombinant apyrase protein within 6 hours of the onset of the ischemic event, wherein the method further comprises carrying out surgical reperfusion therapy (e.g. PCI) on the patient in less than 12 hours, or less than 6 hours, and wherein the $P2Y_{12}$ inhibitor is administered to the patient within 6 hours of administering the recombinant apyrase protein, optionally wherein both the recombinant apyrase protein and the $P2Y_{12}$ inhibitor are administered to the patient before carrying out surgical reperfusion therapy (e.g. PCI).

Any of the methods described herein may further comprise administering aspirin to the patient. Aspirin is typically administered as a separate formulation to the $P2Y_{12}$ inhibitor and recombinant apyrase protein and is administered simultaneously or sequentially to either one or both of the $P2Y_{12}$ inhibitor and recombinant apyrase protein. In some embodiments, aspirin is administered within 24 hours, 18 hours, 12 hours, 6 hours, 2 hours, 1 hour or more preferably within 30 minutes of administering the $P2Y_{12}$ inhibitor. In some embodiments, aspirin is administered within 24 hours, 18 hours, 12 hours, 6 hours, 2 hours, 1 hour or more preferably within 30 minutes of administering the recombinant apyrase protein. In some embodiments, aspirin is administered simultaneously with the $P2Y_{12}$ inhibitor or recombinant apyrase protein. In some embodiments, the aspirin is administered to the patient in conjunction with the $P2Y_{12}$ inhibitor 24 hours or less, or 18 hours or less, or 12 hours or less, or 6 hours or less, or 4 hours or less, or 2 hours or less, or 1 hour or less, or even 30 minutes or less after onset of the ischemic event (e.g. acute coronary syndrome such as STEMI).

Aspirin may be administered to the patient at a dose between 50 mg to 325 mg, or 50 mg to 350 mg, e.g. 50 mg, 75 mg, 100 mg, 125 mg, 150 mg, 162 mg, 175 mg, 200 mg, 225 mg, 250 mg, 275 mg, 300 mg, 325 mg or 350 mg. In some embodiments, aspirin is administered to the patient at a dose between 50 mg and 200 mg, or between 100 mg and 200 mg, e.g. 162 mg. In some embodiments, aspirin is administered to the patient between 200 mg and 350 mg, or between 250 and 325 mg, e.g. 300 mg or 325 mg. In some embodiments, aspirin is administered to the patient at a dose between 75 mg and 150 mg, or between 75 mg and 100 mg.

The term "treatment," as used herein in the context of treating a condition, pertains generally to treatment and therapy of a human, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

Administration of the recombinant apyrase protein described herein may be given by, for example, bolus injection, intravenously, intramuscularly, subcutaneously, inhalation, continuous infusion, sustained release, or other pharmaceutically acceptable techniques. Ideally the recombinant apyrase protein will be administered to patients in a pharmaceutically acceptable form containing physiologically acceptable carriers, excipients or diluents. Such diluents and excipients may be comprised of neutral buffered saline solution, antioxidants (for example ascorbic acid), low molecular weight polypeptides (for example polypeptides<10 amino acids) amino acids, carbohydrates (for example, glucose, dextrose, sucrose, or dextrans), chelating agents such as EDTA, stabilizers (such as glutathione). Additionally, co-substrates for the recombinant apyrase proteins, for example, calcium (Ca 2+) may be administered at time of dosage for maximal activity of the enzyme. Such carriers and diluents are selected to be nontoxic to the patient at recommended dosages and concentrations.

Administration of the $P2Y_{12}$ inhibitor described herein will depend on the particular $P2Y_{12}$ inhibitor being used. For example, ticagrelor, clopidogrel, ticlopidine and prasugrel are typically administered to patients in a pharmaceutically acceptable oral dosage form, while cangrelor is typically administered to patients via intravenous injection.

Dosage requirements of recombinant apyrase proteins may vary significantly depending on age, race, weight, height, gender, duration of treatment, methods of administration, biological activity of recombinant apyrase protein, and severity of condition or other clinical variables. Effective dosages may be determined by a skilled physician or other skilled medical personnel.

The method may comprise administering the recombinant apyrase proteins as a single effective dose in conjunction with a suitable dose (e.g. loading dose) of the $P2Y_{12}$ inhibitor, and optionally aspirin if present. Whilst only a single effective dose of the recombinant apyrase protein is typically used, the method may further comprise administering one or more oral doses of the $P2Y_{12}$ inhibitor periodically and subsequent to the loading dose, as part of a chronic or maintenance treatment. For example, the $P2Y_{12}$ inhibitor may be administered once or twice a day, for weeks, months or even years following the initial loading dose, e.g. at the maintenance doses described above. The maintenance doses of $P2Y_{12}$ inhibitor may be administered with aspirin, as is known in the art. Chronic or maintenance treatment of $P2Y_{12}$ inhibitors following an ischemic event is known in the art and appropriate doses and timing can be determined by a skilled physician or other skilled medical personnel.

The recombinant apyrase protein may be administered as a pharmaceutical composition comprising the recombinant apyrase protein and a pharmaceutically acceptable carrier or diluent. The $P2Y_{12}$ inhibitor may be administered as a pharmaceutical composition comprising the $P2Y_{12}$ inhibitor and a pharmaceutically acceptable carrier or diluent.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example+/−10%.

EXAMPLES

Example 1—Materials and Method for Experiments Performed in Pigs

Experimental Design

Regular chow-fed Landrace pigs (n=20; weight≈40 kg) were randomly (Excel randomized function) distributed into four groups to receive:

I) Oral placebo-control (2 h prior Myocardial Infarction (MI) induction n=5)

II) A loading dose of ticagrelor (180 mg; n=5; p.o 2 h prior MI induction)

III) A loading dose of ticagrelor (180 mg; n=5; p.o 2 h prior MI induction and 1 mg/kg AZD3366 i.v. 10 min before reperfusion)

IV) A loading dose of ticagrelor (180 mg; n=5; p.o 2 h prior MI induction and 3 mg/kg AZD3366 i.v. 10 min before reperfusion)

Thereafter, pigs underwent temporary (90 minutes) balloon occlusion of the mid-left anterior descending coronary artery (experimental MI) and then reperfused, essentially as described in Vilahur et al. 2016. Throughout the following 42 days, the pigs received daily oral maintenance dosing of placebo (group I) or ticagrelor (90 mg/bid, groups II to IV) and serial Cardiac Magnetic Resonance (CMR) assessments were performed at day 3 (early remodeling phase) and day 42 (late remodeling phase) post-MI.

This experimental design is schematically illustrated in FIG. 1.

Experimental Induction of MI

On the day of MI-induction animals received buprenorphine (0.03 mg/kg) and cefazoline (25 mg/kg) as prophylaxis for pain and wound infection, respectively, and then anaesthetized by administrating an intramuscular injection of ketamine (30 mg/kg), xylazine (2.2 mg/kg), and atropine (0.05 mg/kg). Once tranquilized, animals were endotracheally intubated and anesthesia was maintained by isoflurane inhalation (2%). Prior to starting the MI-induction procedure, an infusion of amiodarone (300 mg) and lidocaine (150 mg) in 1.000 mL of saline (250 mL/h) was initiated as prophylaxis for malignant ventricular arrhythmias through a line placed in the marginal ear vein and a bolus of heparin (100 U/kg) was administered to prevent clot formation in the catheters. MI was experimentally induced by a minimally invasive closed chest myocardial balloon occlusion of the mid-portion of the left anterior descending coronary artery as previously described in Vilahur et al. 2016. Complete coronary ischemia (verified by angiography) was maintained for 90 minutes. At the end of the ischemic period, the balloon was completely deflated and animals were allowed to recover. Electrocardiogramand hemodynamic parameters were continuously recorded throughout the entire procedure and the echocardiographic system (Phillips iE33) equipped with a S5-1 sector array transducer was used prior- and post-MI induction to document the initial worsening of left ventricular ejection fraction (LVEF, M-mode analysis using the parasternal long-axis view; Vilahur et al. 2016).

3T-CMR Acquisition and Analysis: Global and Regional Structural and Functional Analyses CMR studies were conducted serially in all animals at Day 3 (early remodeling phase) and Day 42 (late remodeling phase) post-MI. The studies were performed on a 3.0T-CMR system (AchievaVR, Philips, Amsterdam, The Netherlands) and CMR image acquisition was carried out by a CMR specialized technician blinded in terms of treatment. For CMR studies, animals were anaesthetized with an intramuscular injection of a cocktail composed of ketamine, xylazine, and atropine and maintained by a continuous intravenous infusion of propofol to ensure mechanical ventilation. Once the animals were positioned in a head-first supine position with a flexible phased-array surface coil placed over the chest, ECG gating was used to acquire still images of the heart. The following dedicated CMR sequences were acquired in all cases: 'cine' Balanced Steady-State Free Precession (bSSFP) imaging sequence to assess wall motion (WM) and cardiac function; T2-weighted short-tau inversion recovery (T2w-STIR) sequence to assess myocardial edema; early gadolinium enhancement to study microvascular obstruction (no reflow phenomenon); and late gadolinium enhancement (LGE) to assess the amount and extent of myocardial necrosis. All the CMR studies followed the same scheme. First, scout images [T1-turbo field echo (TFE) sequence] were obtained to localize the true axes of the heart and define a field of view involving the whole heart. Afterwards, the bSSFP cine imaging was performed in both horizontal and vertical long axes (four-chamber and two-chamber views) and in multiple contiguous short-axis images covering the whole left ventricle (LV). In the short-axis cine sequence, we acquired 24 cardiac phases of every slice to guarantee a correct evaluation of the WM and heart function. Once the cine sequences were acquired, a T2w-STIR sequence was obtained to assess myocardial edema. Thereafter, a gadolinium-based contrast agent was injected intravenously (Gd-GTPA, MagnevistVR, Berlex Laboratories Inc., Wayne, NJ, USA) at a dose of 0.1 mmol/kg. The early gadolinium enhancement sequence was acquired 1 min after the administration of the contrast. The LGE sequences were obtained 10 min after the administration of contrast. The details of the technical parameters for CMR sequences and the protocol of analysis for global and regional functional/anatomical parameters has been previously published (Vilahur et al. 2016).

Example 2—Effects of AZD3366 and Ticagrelor on Cardiac Damage, Function and Bleeding in Pig Model of Myocardial Infarction An experiment was carried out to examine whether administration of a recombinant soluble form of ADPase, AZD3366 (also termed APT102), confers additional benefits to that of ticagrelor alone in terms of reduced infarct size and improved heart function. The methodology and analysis were performed as set out in Example 1.

Cardiac Damage Assessment

The results of the cardiac damage assessment experiment in the pig animal model are provided in the following tables:

Cardiac damage assessed by CMR 3 Days Post-MI

| | Placebo | Ticagrelor | Ticagrelor + 1 mg/kg AZD3366 | Ticagrelor + 3 mg/kg AZD3366 |
|---|---|---|---|---|
| LV Mass | 70.0 ± 4.1 | 81.3 ± 7.4 | 75.0 ± 3.6 | 76.5 ± 2.2 |
| Edema (gr) | 20.4 ± 1.7 | 10.5 ± 0.8* | 7.3 ± 1.7* | 6.4 ± 0.8*† |
| Edema % of LV mass | 29.8 ± 1.9 | 13.1 ± 0.9* | 9.8 ± 2.3* | 8.4 ± 0.9*† |
| Necrosis (gr) | 12.2 ± 1.5 | 6.6 ± 1.0* | 5.2 ± 0.7* | 3.2 ± 0.9*† |
| Necrosis % of LV mass | 7.7 ± 1.5 | 8.2 ± 1.2* | 7.0 ± 0.9* | 4.2 ± 1.2*† |

*p < 0.05 vs Placebo;
†p < 0.05 vs all the others

Cardiac damage assessed by CMR 42 Days Post-MI

| | Placebo | Ticagrelor | Ticagrelor + 1 mg/kg AZD3366 | Ticagrelor + 3 mg/kg AZD3366 |
|---|---|---|---|---|
| LV Mass | 100.6 ± 3.6 | 108.6 ± 6.9 | 107 ± 6.7 | 111.7 ± 9.4 |
| Necrosis (gr) | 7.9 ± 0.9 | 4.7 ± 1.0* | 4.5 ± 1.7* | 3.4 ± 1.2*† |
| Necrosis % of LV mass | 7.8 ± 0.7 | 4.3 ± 0.8* | 4.1 ± 1.5* | 2.8 ± 1.0*† |

*p < 0.05 vs Placebo;
†p < 0.05 vs all the others

The further reduction in necrotic area in the ticagrelor+3 mg/kg AZD 3366 compared to ticagrelor alone, and the numerical lower necrotic area in the ticagrelor+1 mg/kg AZD3366 demonstrates a dose-dependent enhanced cardio-protective effect of the combination. As this model is the best pre-clinical model for human disease, this is the strongest evidence possible to suggest a therapeutic effect in humans.

Cardiac Function Assessment

The results of the cardiac function assessment experiment in the pig animal model are provided in the following tables:

Global and regional cardiac function assessed by CMR

| | Time | Placebo | Ticagrelor | Ticagrelor + 1 mg/kg AZD3366 | Ticagrelor + 3 mg/kg AZD3366 |
|---|---|---|---|---|---|
| LVEF % | BSL | 58.7 ± 2.1 | 53.7 ± 2.8 | 55.4 ± 1.4 | 52.8 ± 2.2 |
| | 3 Days | 48.6 ± 2.0* | 50.3 ± 2.9 | 46.4 ± 2.0 | 52.0 ± 3.5 |
| | 42 Days | 46.2 ± 3.0* | 47.0 ± 4.4 | 46.6 ± 5.5 | 54.8 ± 3.8 |

*p < 0.05 vs BSL (baseline)

Global and regional cardiac function assessed by CMR

| | Time | Placebo | Ticagrelor | Ticagrelor + 1 mg/kg AZD3366 | Ticagrelor + 3 mg/kg AZD3366 |
|---|---|---|---|---|---|
| Wall | BSL | 2.81 | 2.66 | 2.63 | 2.75 |
| motion | 3 Days | 1.11 | 1.88 | 1.73 | 2.68* |
| (mm) | 42 Days | 1.82 | 2.55 | 2.64 | 3.09* |

*$p < 0.05$ vs all the others

The further improvement in wall motion score in the ticagrelor+3 mg/kg AZD 3366 compared to ticagrelor alone, is demonstrating an enhanced healing and recovery of cardiac function following myocardial infarction. The simultaneous occurrence of reduced infarct size and improved function is linking the acute cardioprotective mode-of-action to an improved functional recovery of the heart. As this model is the best pre-clinical model for human disease, this is the strongest evidence possible to suggest a therapeutic effect in humans.

Example 3—Effects of AZD3366 and Ticagrelor on Mouse Tail Bleeding

The aim of this study was to evaluate the bleeding risk and platelet aggregation inhibition of AZD3366 alone or in combination with ticagrelor in mice in vivo.

Experimental Protocol

C57BI6 mice were administered an intravenous bolus of AZD3366 or vehicle. In separate groups, mice were administered AZD3366 and ticagrelor or ticagrelor only as a bolus and continuous infusion of ticagrelor. The groups, doses and volumes of administration were as described in the following table:

| | | Dose | | Volume | |
|---|---|---|---|---|---|
| Group | Treatment | Bolus (mg/kg) | Infusion (μg/kg*min) | Bolus (mL/kg) | Infusion (μL/kg*min) |
| Vehicle (V) | 5% mannitol + buffer | NA | NA | 1.0 + 1.0 | 200 + NA |
| Ticagrelor (T) | ticagrelor + buffer | 1.2 + NA | 30 + NA | 1.0 + 1.0 | 200 + NA |
| AZD3366 (AZD1) | 5% mannitol + AZD3366 | NA + 1.0 | NA + NA | 1.0 + 1.0 | 200 + NA |
| AZD3366 (AZD3) | 5% mannitol + AZD3366 | NA + 3.0 | NA + NA | 1.0 + 1.0 | 200 + NA |
| Ticagrelor + AZD3366 (T + AZD1) | ticagrelor + AZD3366 | 1.2 + 1.0 | 30 + NA | 1.0 + 1.0 | 200 + NA |

Buffer = 20 mmol/L Tris, 150 mmol/L NaCl, pH 7.4. NA; Not Applicable. Twelve animals were included in each study group.

At t = 20 min, the tail transection was made and blood loss and bleeding time (BT) were recorded for 60 min. At the end of the experiment, t = 80 min, a blood sample from the abdominal aorta for platelet aggregation assessment and subsequent plasma concentration analysis of AZD3366 and ticagrelor was collected.

Bleeding Model

Twenty min following dosing, bleeding was initiated by cutting 5 mm of the tip of the tail. The tail was rinsed with water and placed in a haemoglobin sensitive device. Light transmission through the blood and water mixture was recorded and converted to absorbance using the PharmLab software (V6.0, AstraZeneca R&D, Gothenburg, Sweden). Transmittance below 95% was defined as bleeding. Total blood loss, (area under the bleeding curve, t=20 min to t=80 min: cumulative blood loss vs time, absorbance*s, abs*s) and bleeding time (BT) were measured over 60 min from the start of tail cutting.

Blood and Plasma Analysis

The blood sample from the abdominal aorta was collected in an Omnifix®-F 1 ml syringe (Braun Medical AG, Emmenbrücke, Germany) together with a Terumo® Neolus 27G, 0.4×20 mm needle (Terumo Europe N.V., Leuven Belgium). Lepirudin (Refludan® Bayer HealthCare Pharmaceuticals Inc), 10 μL, 5 mg/mL to a maximum of 1 mL blood, which gives a final blood concentration of 7 μmol/L, was used as anticoagulant. Whole blood was used for platelet aggregation using the Multiplate® impedance aggregometer. Plasma was prepared from the remaining blood by centrifugation at 10000*g for 5 min (Ole Dich, Hvidovre, Denmark). Plasma was transferred to new tubes and stored at −20° C. for later analysis of total plasma concentration of ticagrelor and AZD3366.

Immediately after the blood sampling, 175 μL whole blood was added to the Multiplate® (Roche Diagnostics GmbH, Mannheim, Germany) mini test cells and mixed with 175 μL 37° C. pre-heated saline (9 mg/mL, Fresenius Kabi AG, Bad Homburg, Germany). After 3 min, 12 μL adenosine diphosphate (ADP, Roche Diagnostics, Mannheim, Germany) was added to a final assay concentration of 6.5 μmol/L. The response was measured for 6 min and data is expressed as the mean area under the curve (AUC) of aggregation unit (AU) recorded over time (AU*min).

The plasma concentration of ticagrelor was determined by means of a Liquid Chromatographic-Mass Spectrometric (LC-MS/MS) method.

The plasma concentration of AZD3366 was determined by ELISA involving capture of AZD3366 with monoclonal mouse anti-AZD3366 antibody (mAb2567, Covance, Princeton, NJ, USA) coated on 96-well plates and detection of bound AZD3366 with horseradish peroxidase-conjugated polyclonal rabbit anti-AZD3366 antibody (pAb3939-HRP, Covance) using TMB as the substrate.

Results

Results for blood loss and BT are presented in the table below and illustrated in FIG. 2.

Blood loss and bleeding time (BT)

| Group | Blood loss (abs*s) Median | Blood loss (abs*s) Range (min-max) | BT (s) Median | BT (s) Range (min-max) |
|---|---|---|---|---|
| Vehicle | 160 | 28-778 | 655 | 66-2734 |
| Ticagrelor | 1157a, b, c | 139-1542 | 3433a, d | 420-3587 |
| AZD3366 1.0 mg/kg | 157 | 34-1415 | 589 | 107-3582 |
| AZD3366 3.0 mg/kg | 342e | 52-1072 | 1438 | 268-2931 |
| Ticagrelor + AZD3366 1.0 mg/kg | 961 | 176-1464 | 2657 | 930-3585 |

Blood loss and BT in ticagrelor-treated animals increased 7.2-fold ($p<0.001$) and 5.2-fold ($p<0.001$) as compared to animals administered vehicle, respectively. In contrast, treatment with AZD3366 at 1 or 3 mg/kg was not associated with a statistically significant increase in blood loss or BT vs vehicle. Furthermore, blood loss and BT in the combined ticagrelor and AZD3366 group did not differ as compared to that seen in the group of animals administered ticagrelor only.

The platelet aggregation (PA) results are set out in the following table:

Platelet aggregation inhibition and plasma concentration of AZD3366 (AZD) and ticagrelor (T) in the mouse

| Group | PA (AU*min) | T (μmol/L) | AZD (μg/mL) |
|---|---|---|---|
| Vehicle | 469 ± 34 | — | — |
| T | 2 ± 2 | 8 ± 0.2 | — |
| AZD1 | 2 ± 2 | — | 20 ± 1.9 |
| AZD3 | 0 ± 0 | — | 66 ± 2.5 |
| T + AZD1 | 0 ± 0 | 8 ± 0.3 | 20 ± 0.7 |

Figure 2:
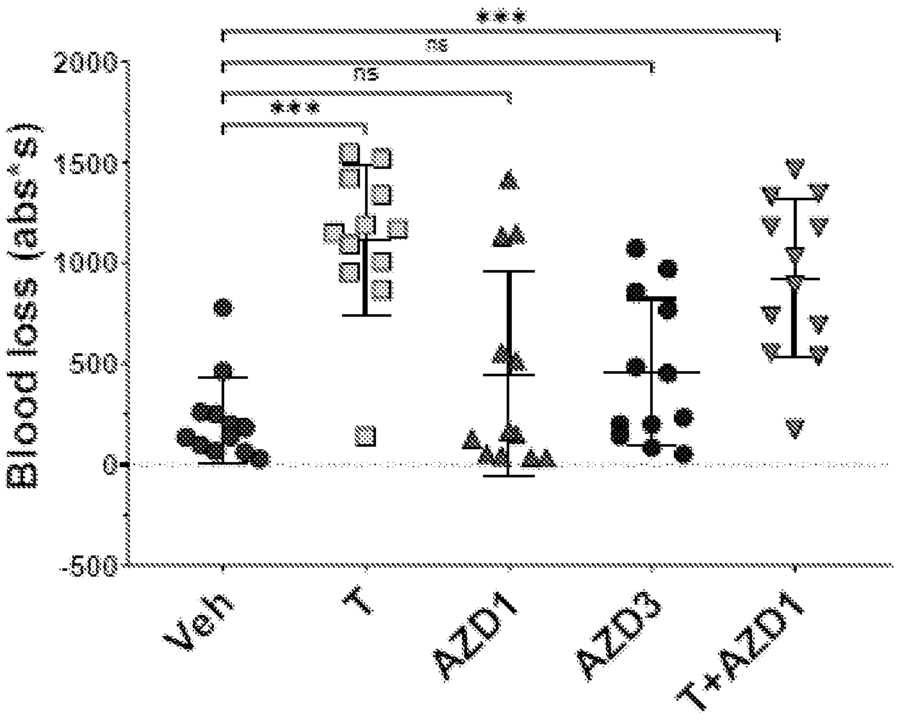
FIG. 2 shows results obtained from a mouse tail bleeding experiment showing the amount of blood loss measured following administration with ticagrelor (T), 1 mg/kg AZD3366 (AZD1), 3 mg/kg AZD3366 (AZD3) and the combined administration of AZD3366 and ticagrelor (T+AZD1). The results demonstrate that the combined administration of AZD3366 and ticagrelor did not increase blood loss above that seen for ticagrelor alone (T). Shown are means±SEM. ns; not significant, ***; P<0.001 (one-way ANOVA+Dunnet's multiple comparison test).

Thus, in contrast to ticagrelor (T), complete platelet aggregation (PA) inhibition by AZD3366 (1 and 3 mg/kg) was not associated with increased bleeding (FIG. 2). In addition, combined dosing of AZD3366 and ticagrelor did not increase bleeding above that seen for ticagrelor alone.

Results from this experiment demonstrate that the combination of ticagrelor and AZD3366 does not increase bleeding above that seen for ticagrelor alone.

REFERENCES

A number of publications are cited above in order to more fully describe and disclose the invention and the state of the art to which the invention pertains. Full citations for these references are provided below. The entirety of each of these references is incorporated herein.

Asaria, P., Elliott, P., Douglass, M., Obermeyer, Z., Soljak, M., Majeed, A., & Ezzati, M. (2017). Acute myocardial infarction hospital admissions and deaths in England: a national follow-back and follow-forward record-linkage study. *The Lancet. Public health,* 2(4), e191-e201.

Ibanez, B., James, S., Agewall, S., Antunes, M. J., Bucciarelli-Ducci, C., Bueno, H., Caforio, A., Crea, F., Goudevenos, J. A., Halvorsen, S., Hindricks, G., Kastrati, A., Lenzen, M. J., Prescott, E., Roffi, M., Valgimigli, M., Varenhorst, C., Vranckx, P., Widimský, P., & ESC Scientific Document Group (2018). 2017 ESC Guidelines for the management of acute myocardial infarction in patients presenting with ST-segment elevation: The Task Force for the management of acute myocardial infarction in patients presenting with ST-segment elevation of the European Society of Cardiology (ESC). *European heart journal,* 39(2), 119-177.

Jernberg, T., Hasvold, P., Henriksson, M., Hjelm, H., Thuresson, M., & Janzon, M. (2015). Cardiovascular risk in post-myocardial infarction patients: nationwide real world data demonstrate the importance of a long-term perspective. *European heart journal,* 36(19), 1163-1170.

Robson, S. C., Wu, Y., Sun, X., Knosalla, C., Dwyer, K., & Enjyoji, K. (2005). Ectonucleotidases of CD39 family modulate vascular inflammation and thrombosis in transplantation. *Seminars in thrombosis and hemostasis,* 31(2), 217-233.

Sun, Guanghua & Zhao, Xiurong & Grotta, James & Savitz, Sean & Chen, Ridong & Aronowski, Jaroslaw. (2011). Apyrase, APT102, Improves the Beneficial Effect of rt-PA In Experimental Thromboembolic Stroke. E302-E302.

Tan, Z., Li, X., Turner, R. C., Logsdon, A. F., Lucke-Wold, B., DiPasquale, K., Jeong, S. S., Chen, R., Huber, J. D., & Rosen, C. L. (2014). Combination treatment of r-tPA and an optimized human apyrase reduces mortality rate and hemorrhagic transformation 6h after ischemic stroke in aged female rats. *European journal of pharmacology,* 738, 368-373.

Thygesen, K., Alpert, J. S., Jaffe, A. S., Chaitman, B. R., Bax, J. J., Morrow, D. A., White, H. D., & Executive Group on behalf of the Joint European Society of Cardiology (ESC)/American College of Cardiology (ACC)/American Heart Association (AHA)/World Heart Federation (WHF) Task Force for the Universal Definition of Myocardial Infarction (2018). Fourth Universal Definition of Myocardial Infarction (2018). *Circulation,* 138(20), e618-e651.

Vilahur G, Gutierrez M, Casani L, Varela L, Capdevila A, Pons-Llado G, Carreras F, Carlsson L, Hidalgo A, Badimon L. Protective effects of ticagrelor on myocardial injury after infarction. *Circulation* 2016; 134: 1708-1719.

Wallentin, L., Becker, R. C., Budaj, A., Cannon, C. P., Emanuelsson, H., Held, C., Horrow, J., Husted, S., James, S., Katus, H., Mahaffey, K. W., Scirica, B. M., Skene, A., Steg, P. G., Storey, R. F., Harrington, R. A., PLATO Investigators, Freij, A., & Thorsén, M. (2009). Ticagrelor versus clopidogrel in patients with acute coronary syndromes. *The New England journal of medicine,* 361(11), 1045-1057.

For standard molecular biology techniques, see Sambrook, J., Russel, D. W. *Molecular Cloning, A Laboratory Manual.* 3 ed. 2001, Cold Spring Harbor, New York: Cold Spring Harbor Laboratory Press Sequences

| Identifier | Description | Sequence |
|---|---|---|
| SEQ ID NO: 1 | Human CD39L3 amino acid sequence (amino acid residues 49-485 of SEQ ID NO: 1 bold) | MVTVLTRQPCEQAGLKALYRTPTIIALVVLLVSIVVLVSITVIQIHK<br>Q**EVLPPGLKYGIVLDAGSSRTTVYVYQWPAEKENNTGVVSQTEKCSV**<br>**KGSGISSYGNNPQDVPRAFEECMQKVKGQVPSHLHGSTPIHLGATAG**<br>**MRLLRLQNETAANEVLESIQSYFKSQPFDFRGAQIISGQEEGVYGWI**<br>**TANYLMGNFLEKNLWHMWVHPHGVETTGALDLGGASTQISFVAGEKM**<br>**DLNTSDIMQVSLYGYVYTLYTHSFQCYGRNEAEKKFLAMLLQNSPTK**<br>**NHLTNPCYPRDYSISFTMGHVFDSLCTVDQRPESYNPNDVITFEGTG**<br>**DPSLCKEKVASIFDFKACHDQETCSFDGVYQPKIKGPFVAFAGFYYT**<br>**ASALNLSGSFSLDTENSSTWNFCSQNWSQLPLLLPKFDEVYARSYCF**<br>**SANYIYHLFVNGYKFTEETWPQIHFEKEVGNSSIAWSLGYMLSLTNQ**<br>**IPAESPLIRLPIEPP**VFVGTLAFFTAAALLCLAFLAYLCSATRRKRH<br>SEHAFDHAVDSD |
| SEQ ID NO: 2 | AZD3366 amino acid sequence (N-terminal EVLP bold, R67G and T69R amino acid substitutions bold italics) | **EVLP**PGLKYGIVLDAGSS***G***T***R***VYVYQWPAEKENNTGVVSQTFKCSVK<br>GSGISSYGNNPQDVPRAFEECMQKVKGQVPSHLHGSTPIHLGATAGM<br>RLLRLQNETAANEVLESIQSYFKSQPFDFRGAQIISGQEEGVYGWIT<br>ANYLMGNFLEKNLWHMWVHPHGVETTGALDLGGASTQISFVAGEKMD<br>LNTSDIMQVSLYGYVYTLYTHSFQCYGRNEAEKKFLAMLLQNSPTKN<br>HLTNPCYPRDYSISFTMGHVEDSLCTVDQRPESYNPNDVITFEGTGD<br>PSLCKEKVASIFDFKACHDQETCSFDGVYQPKIKGPFVAFAGFYYTA<br>SALNLSGSFSLDTENSSTWNFCSQNWSQLPLLLPKFDEVYARSYCES<br>ANYIYHLFVNGYKFTEETWPQIHFEKEVGNSSIAWSLGYMLSLTNQI<br>PAESPLIRLPIEPPV |

The invention claimed is:

1. A method of treating an ischemic event in a patient, the method comprising sequentially or simultaneously administering to the patient a recombinant apyrase protein comprising the amino acid sequence of SEQ ID NO: 2 and ticagrelor, wherein the ischemic event is ST-segment elevation myocardial infarction (STEMI).

2. The method according to claim 1, wherein the method comprises administering the recombinant apyrase protein to the patient, followed by the sequential administration of ticagrelor; or administering ticagrelor to the patient, followed by the sequential administration of the recombinant apyrase protein.

3. The method according to claim 1, wherein the recombinant apyrase protein is administered to the patient within 24 hours or within 12 hours of ticagrelor the being administered to the patient.

4. The method according to claim 1, wherein the method further comprises at least daily administrations of ticagrelor to the patient starting at least 24 hours after the recombinant apyrase protein and ticagrelor are administered to the patient.

5. The method according to claim 1, wherein the recombinant apyrase protein is administered at a dose of 10 mg to 1000 mg.

6. The method according to claim 1, wherein:

ticagrelor is administered at a dose of between 60 to 200 mg.

7. The method according to claim 1, wherein the method further comprises administering aspirin to the patient.

8. The method according to claim 1, wherein the recombinant apyrase protein is sequentially or simultaneously administered to the patient in with ticagrelor 24 hours or less, 12 hours or less, or 6 hours or less after onset of the ischemic event.

9. The method according to claim 6, wherein ticagrelor is administered at a dose of 180 mg.

10. The method according to claim 7, wherein the aspirin is administered at a dose of 50 mg to 325 mg.

* * * * *

SEQUENCE LISTING

```
Sequence total quantity: 2
SEQ ID NO: 1           moltype = AA  length = 529
FEATURE                Location/Qualifiers
source                 1..529
                       mol_type = protein
                       organism = Homo sapiens
SEQUENCE: 1
MVTVLTRQPC EQAGLKALYR TPTIIALVVL LVSIVVLVSI TVIQIHKQEV LPPGLKYGIV  60
LDAGSSRTTV YVYQWPAEKE NNTGVVSQTF KCSVKGSGIS SYGNNPQDVP RAFEECMQKV  120
KGQVPSHLHG STPIHLGATA GMRLLRLQNE TAANEVLESI QSYFKSQPFD FRGAQIISGQ  180
EEGVYGWITA NYLMGNFLEK NLWHMWVHPH GVETTGALDL GGASTQISFV AGEKMDLNTS  240
DIMQVSLYGY VYTLYTHSFQ CYGRNEAEKK FLAMLLQNSP TKNHLTNPCY PRDYSISFTM  300
GHVFDSLCTV DQRPESYNPN DVITFEGTGD PSLCKEKVAS IFDFKACHDQ ETCSFDGVYQ  360
PKIKGPFVAF AGFYYTASAL NLSGSFSLDT FNSSTWNFCS QNWSQLPLLL PKFDEVYARS  420
YCFSANYIYH LFVNGYKFTE ETWPQIHFEK EVGNSSIAWS LGYMLSLTNQ IPAESPLIRL  480
PIEPPVFVGT LAFFTAAALL CLAFLAYLCS ATRRKRHSEH AFDHAVDSD             529

SEQ ID NO: 2           moltype = AA  length = 438
FEATURE                Location/Qualifiers
REGION                 1..438
                       note = Synthetic
source                 1..438
                       mol_type = protein
                       organism = synthetic construct
SEQUENCE: 2
EVLPPGLKYG IVLDAGSSGT RVYVYQWPAE KENNTGVVSQ TFKCSVKGSG ISSYGNNPQD  60
VPRAFEECMQ KVKGQVPSHL HGSTPIHLGA TAGMRLLRLQ NETAANEVLE SIQSYFKSQP  120
FDFRGAQIIS GQEEGVYGWI TANYLMGNFL EKNLWHMWVH PHGVETTGAL DLGGASTQIS  180
FVAGEKMDLN TSDIMQVSLY GYVYTLYTHS FQCYGRNEAE KKFLAMLLQN SPTKNHLTNP  240
CYPRDYSISF TMGHVFDSLC TVDQRPESYN PNDVITFEGT GDPSLCKEKV ASIFDFKACH  300
DQETCSFDGV YQPKIKGPFV AFAGFYYTAS ALNLSGSFSL DTFNSSTWNF CSQNWSQLPL  360
LLPKFDEVYA RSYCFSANYI YHLFVNGYKF TEETWPQIHF EKEVGNSSIA WSLGYMLSLT  420
NQIPAESPLI RLPIEPPV                                               438
```